United States Patent
Børresen et al.

(10) Patent No.: US 11,474,062 B2
(45) Date of Patent: Oct. 18, 2022

(54) CHARACTERISATION OF EMULSION STABILITY

(71) Applicant: Equinor Energy AS, Stavanger (NO)

(72) Inventors: Børre Tore Børresen, Heimdal (NO); Morten Tande, Langesund (NO); Ketil Pettersen, Porsgrunn (NO)

(73) Assignee: Equinor Energy AS, Stavanger (NO)

( * ) Notice: Subject to any disclaimer, the term of this patent is extended or adjusted under 35 U.S.C. 154(b) by 402 days.

(21) Appl. No.: 16/490,414

(22) PCT Filed: Mar. 1, 2017

(86) PCT No.: PCT/NO2017/050058
§ 371 (c)(1),
(2) Date: Aug. 30, 2019

(87) PCT Pub. No.: WO2018/160068
PCT Pub. Date: Sep. 7, 2018

(65) Prior Publication Data
US 2020/0072776 A1    Mar. 5, 2020

(51) Int. Cl.
*G01N 27/06* (2006.01)
*G01N 13/00* (2006.01)
(Continued)

(52) U.S. Cl.
CPC ............... *G01N 27/06* (2013.01); *C09K 8/36* (2013.01); *G01N 13/00* (2013.01); *G01N 33/2847* (2013.01)

(58) Field of Classification Search
CPC .... G01N 27/06; G01N 13/00; G01N 33/2847; G01N 27/02; G01N 27/04; G01N 27/92;
(Continued)

(56) References Cited

U.S. PATENT DOCUMENTS

| | | | |
|---|---|---|---|
| 4,134,799 A | 1/1979 | Allen et al. | |
| 4,863,572 A * | 9/1989 | Jasinski | G01N 17/02 205/775.5 |

(Continued)

FOREIGN PATENT DOCUMENTS

| | | |
|---|---|---|
| CN | 102954983 A | 3/2013 |
| CN | 105699428 A | 6/2016 |

(Continued)

OTHER PUBLICATIONS

Sep. 28, 2017—(WO) International Search Report and Written Opinion—App PCT/NO2017/050058.
(Continued)

*Primary Examiner* — Christopher P McAndrew
*Assistant Examiner* — Zannatul Ferdous
(74) *Attorney, Agent, or Firm* — Banner & Witcoff, Ltd.

(57) ABSTRACT

A method of assessing the effect of a production chemical on the stability of a water and oil emulsion, the emulsion comprising the production chemical, is provided. The method comprises: applying a potential difference across the emulsion at a detection site; measuring a current flowing through the emulsion due to the applied potential difference; and using this measured current to assess the effect of the production chemical. The step of using the measured current to assess the effect of the production chemical may comprise determining, based on the measured current, whether a critical potential of the emulsion has been reached or exceeded. The emulsion may be a crude oil emulsion. It may be a water-in-oil emulsion. The production chemical may be an emulsion breaker. Also provided is an apparatus for assessing the effect of a production chemical on a water and oil emulsion.

18 Claims, 4 Drawing Sheets

(51) Int. Cl.
*G01N 33/28* (2006.01)
*C09K 8/36* (2006.01)

(58) Field of Classification Search
CPC .. C09K 8/36; C09K 2208/24; C09K 2208/26; C09K 2208/32
See application file for complete search history.

(56) References Cited

U.S. PATENT DOCUMENTS

| | | | |
|---|---|---|---|
| 10,197,546 B2* | 2/2019 | Rahaliou | G01N 33/2847 |
| 2006/0278584 A1* | 12/2006 | Bowden | B03C 3/017 |
| | | | 210/739 |
| 2010/0180663 A1* | 7/2010 | Sun | G01N 33/2888 |
| | | | 73/1.02 |
| 2014/0062489 A1 | 3/2014 | Pindiprolu et al. | |
| 2019/0055450 A1* | 2/2019 | Mohammed | C09K 8/36 |
| 2019/0055841 A1* | 2/2019 | Brady | E21B 47/113 |

FOREIGN PATENT DOCUMENTS

| | | |
|---|---|---|
| CN | 205786427 U | 12/2016 |
| RU | 2184205 C2 | 6/2002 |

OTHER PUBLICATIONS

Sjöblom et al., Advances in Colloid and Interface Science, 100-102 (2003) 449-450.

Silset, Anne, "Emulsions (w/o and o/w) of Heavy Crude Oils. Characterization, Stabilization, Destabilization and Produced Water Quality", PhD Thesis, Norwegian University of Science and Technology, Nov. 2008.

Wise, Barry M. et al., "The process chemometrics approach to process monitoring and fault detection", J. Proc. Cont., vol. 6, No. 6, pp. 329-348, 1996.

Kallevik, Harald, et al., "Quantitative Determination of Asphaltenes and Resins in Solution by Means of Near-Infrared Spectroscopy. Correlations to Emulsion Stability", Journal of Colloid and Interface Science 225, 494-504, (2000).

Sjöblom, Johan et al., "Our current understanding of water-in-crude oil emulsions. Recent characterization techniques and high pressure performance", Advances in Colloid and Interface Science 100-102 (2003) 399-473.

Azizi, K. et al., "Characterization of Chemical Demulsification of Oil in Water Emulsion: Comparison Between a Kinetics Model and Laboratory Experiments", Petroleum Science and Technology, 33:8-14, 2015.

"Emulsions and Emulsion Stability" (Second Edition), Edited By Johann Sjöblom, University of Bergen, Norway, Taylor & Francis Group, LLC, 2006.

Tadros, Tharwat F., "Emulsion Formation and Stability", First Edition, Chapter 1: "Emulsion Formation, Stability, and Rheology", p. 1-76, Wiley, 2013.

Wang, Xiuyu et al., "Direct Current Electrorheological Stability Determination of Water-in-Crude Oil Emulsions", J. Phys. Chem. B 2009, 113, 13811-13816.

Jun. 23, 2021—(CN) First Office Action—APP 201780090075.5.
Sep. 13, 2021—(GB) Examination Report—APP GB1912802.4.
May 13, 2022 (CN) Third Office Action Application No. 201780090075.5.

* cited by examiner

CHARACTERISATION OF EMULSION STABILITY

The present application is a U.S. National Phase of International Application No. PCT/NO2017/050058, filed on Mar. 1, 2017, designating the United States of America. This application claims priority to and the benefit of the above-identified application, which is fully incorporated by reference herein in its entirety.

The present invention relates to the characterisation of emulsion stability. In particular, it relates to methods and apparatuses for assessing the effect of a production chemical, for example an emulsion breaker, on the emulsion stability of a water and oil emulsion, preferably crude oil emulsions.

Water-in-oil and oil-in-water emulsions can form at all stages during the production and processing of crude oil, from the reservoir and wellhead through to separation and storage. These emulsions must be resolved (i.e. the water and oil must be separated) to provide an end product of the desired quality.

Water-in-oil emulsions are stabilised by interfacial films that form around the water droplets at the oil/water interface. Components in these films enhance the stability of an emulsion by increasing the interfacial viscosity. Emulsion separation into oil and water requires the destabilisation of these emulsifying films. Emulsion breakers (demulsifiers) can be added to aid in the destabilisation of these films and ultimately enhance the separation of emulsions.

Other production chemicals may be added to the process stream containing the water-in-oil emulsions, including corrosion inhibitors and biocides. These production chemicals may affect the stability of an emulsion if they are surface active and act directly on the water/oil mixture, or may interact with and reduce or increase the efficiency of emulsion breakers which have been added to the emulsion.

Various methods are known for determining the stability of emulsions to which emulsion breakers have been added, including:
1. Bottle tests, whereby the demulsifier is added to an emulsion, the mixture is shaken to disperse the demulsifier, and the time for phase separation is recorded.
2. A technique based on light scattering in crude-oil emulsions to measure the coalescence of water droplets in order to determine the emulsion stability. The method can be used to monitor the coalescence action of demulsifiers.
3. Measurement of the dielectric constant of emulsions as a measure of their stability. A change in dielectric constant with time or demulsifier dosage can be used as a measure of the emulsion stability.

The first two of these techniques are not well suited for real-time characterisation of emulsions during processing of the crude oil, while the third technique requires an advanced apparatus for analysing the frequency response. When imaging, the dark color of the crude oil systems presents a challenge. Further, it is difficult to ascertain the efficiency of a particular emulsion breaker using these methods.

Viewed from a first aspect, the invention provides a method of assessing the effect of a production chemical on the stability of a water and oil emulsion, the emulsion comprising the production chemical, wherein the method comprises: applying a potential difference across the emulsion at a detection site; measuring a current flowing through the emulsion due to the applied potential difference; and using this measured current to provide an indication of the stability of the emulsion and thereby assess the effect of the production chemical.

Thus, the emulsion is an emulsion of water and oil. The water and oil emulsion may be a crude oil emulsion. It may be a water-in-oil emulsion. Preferably, it is a water-in-oil crude oil emulsion.

A technique recently developed for measuring emulsion stability of oil/water emulsions is discussed in Sjöblom et al., *Advances in Colloid and Interface Science*, 100-102 (2003) 449-450. This involves determining the electric field required to cause coalescence of an emulsion. A high electric field is applied via a pair of electrodes, to an emulsion to cause flocculation and coalescence of the water in the oil phase, such that the water droplets that are surrounded by the rigid interfacial film attain a chain-like configuration. The emulsion has a very low conductivity before the water droplets align in the electric field, but as the field strength is increased, the water droplets bridge the gap between the electrodes and create a passage for current. Eventually, the interfacial film is irreversibly ruptured and the conductivity of the emulsion significantly increases. The electric field at which this occurs ($E_{critical}$) can therefore become an indicator of the stability of the emulsion. A larger value of $E_{critical}$ is a reflection of a more stable dispersion, since a larger electric field is required to align the water droplets to achieve electrical conduction.

The electric field strength is the potential difference divided by the distance between the electrodes. Thus, where the separation distance of the electrodes is constant, the electric field is proportional to the potential difference across the electrodes. As such, the potential difference at which the conductivity of the emulsion increases, i.e. the critical potential $V_{critical}$, corresponding to the $E_{critical}$, can be used as an indicator of the stability of the emulsion.

The present inventors recognised that such a technique may be developed for the assessment of the effect of a production chemical in a water and oil emulsion, as set out in the first aspect of the invention above, leading to significant advantages over the prior art methods discussed earlier, particularly in terms of crude oil processing.

Firstly, since no samples have to be taken physically from the process stream, the methodology is well suited for remote operation and process control.

Furthermore, the method enables real time measurements of the properties of the emulsion to be taken, which is highly advantageous in terms of process control. Because the effect of the production chemical can be easily assessed in real-time, it can be determined in real-time whether changes need to be made to e.g. the dose or type of production chemical. Thus, the invention facilitates a short response time for correcting actions e.g. adjusting a dosage of a production chemical added to the emulsion.

Such efficient control of the emulsion stability facilitates careful control of dosage of production chemicals being added to the emulsion, and hence avoids waste of chemicals.

The production chemical may be any type of production chemical used which affects the stability of the emulsion, such as an emulsion breaker, corrosion inhibitor, biocide or scale inhibitor. Such production chemicals may affect the stability of the emulsion directly by being surface active and acting directly on the water/oil mixture, or may indirectly affect the emulsion properties by interacting with or reducing the efficiency of another production chemical present.

The concept of the invention is independent of the type of emulsion or production chemical used. Hence it may be used to optimise the amount of production chemical (e.g. emulsion breaker) for a given crude oil and water composition.

It will be appreciated that a "detection site" refers to a location at which the emulsion is examined, for example if the emulsion is flowing a pipeline, then the detection site may be a particular location on the pipeline.

Preferably, the step of using the measured current to provide an indication of the stability of the emulsion includes determining, based on the measured current, whether a critical potential of the emulsion has been reached or exceeded. Thus, the critical potential may be used for on-line real-time monitoring of the effect of the production chemical, which can in turn be used for process control. Process changes which increase the stability of the emulsion will cause a shift in the critical potential to higher values, whilst destabilisation would lead to an opposite effect.

In one embodiment the measured current is compared with a reference current corresponding to the critical potential ($V_{critical}$), and if the measured current is greater than the reference current, it is determined that the critical potential of the emulsion has been reached or exceeded; and if the measured current is less than the reference current it is determined that the critical potential has not been reached or exceeded. It can therefore be considered that in a second aspect, the invention provides a method of assessing the effect of a production chemical on the stability of a water and oil emulsion, the emulsion comprising the production chemical, wherein the method comprises: applying a potential difference across the emulsion at a detection site; measuring a current flowing through the emulsion due to the applied potential difference; and determining, based on the measured current, that a critical potential of the emulsion has been reached or exceeded when the measured current is greater than a reference current that corresponds to the critical potential, to thereby assess the effect of the production chemical on the stability of the emulsion.

In another embodiment, after the step of measuring the current flowing through the emulsion, the method further comprises: increasing the potential difference across the emulsion; measuring the current flowing through the emulsion due to the increased potential difference; and determining the rate of change of current with respect to potential difference; wherein it is determined that the critical potential of the emulsion has been reached or exceeded when the rate of change of current with respect to potential difference is equal to or greater than a reference rate of change value.

Thus, in a third aspect, the invention may be considered as providing a method of assessing the effect of a production chemical on the stability of a water and oil emulsion, the emulsion comprising the production chemical, wherein the method comprises: applying a potential difference across the emulsion at a detection site; measuring a current flowing through the emulsion due to the applied potential difference; increasing the potential difference across the emulsion, measuring the current flowing through the emulsion due to the increased potential difference; and determining the rate of change of current with respect to potential difference; wherein it is determined that the critical potential of the emulsion has been reached or exceeded when the rate of change of current with respect to potential difference is equal to or greater than a reference rate of change value, to thereby assess the effect of the production chemical on the stability of the emulsion.

It will be appreciated that reached or exceeded means that the potential applied to the emulsion is at or above the critical potential of the emulsion.

If it has been determined that the critical potential of the emulsion has not been reached, the above methods may further comprise the step of increasing the potential difference across the emulsion at the detection site, and repeating the steps of: measuring a current flowing through the emulsion due to the applied potential difference, and using this measured current to provide an indication of the stability of the emulsion by determining, based on the measured current, whether a critical potential of the emulsion has been reached or exceeded. The method may then be repeated until the critical potential has been reached or exceeded. The method may be repeated for a predefined range of applied potential difference values, in other words a range of potential differences are "swept". These applied potential difference values preferably increase in increments of between 1 and 100V.

If it has been determined that the critical potential of the emulsion has been reached or exceeded, the above methods may further comprise the steps of determining the critical potential based on the applied potential difference at the time when it was determined that the critical potential has been reached or exceeded; and comparing the critical potential of the emulsion with a reference critical potential to provide an indication of the stability of the emulsion and thereby the effect of the production chemical.

In one embodiment, if the critical potential corresponds to the reference critical potential or falls within a reference window around the reference critical potential, it is determined that the stability of the emulsion is at a desired level and thereby the production chemical is providing the correct effect. If the critical potential is above the reference critical potential or is above a reference window around the reference critical potential it is determined that the stability of the emulsion is too high and the production chemical is not effective enough at breaking the emulsion. If the critical potential is below the reference critical potential or is below a reference window around the reference critical potential it is determined that the stability of the emulsion is too low and the production chemical is too effective at breaking the emulsion. In this latter case however that the stability of the emulsion is too low, in some cases this may in fact be the desired effect, so may alternatively be considered as being "desirably low".

The effect of the production chemical on the stability of the emulsion is thereby assessed and understood. In the case of the production chemical being an emulsion breaker, the efficiency of the emulsion breaker can thereby be appreciated. Embodiments can thus be envisaged where the method of the invention is carried out for different production chemicals, different combinations of production chemicals, and different quantities of production chemicals in order to assess the effect of these different options on the stability of the emulsion, and thereby characterise the effect of the production chemicals.

By a "reference window around the reference critical potential" is meant a range of values below and/or above the reference critical potential which is considered to be close enough to the reference critical potential to be representative of the reference critical potential.

As discussed above, the critical potential is the applied potential difference at which the water droplets align and the conductivity of the emulsion significantly increases. The skilled person would readily be able to define a reference current or reference rate of change of current corresponding to such a critical potential, and thus the critical potential, as appropriate for the particular application. The skilled person would also be readily able to define a reference critical potential indicative of a preferred stability of the emulsion, depending on the particular desired characteristics of the emulsion and the particular application.

It will be appreciated from the earlier description that it is the electric field created by the applied potential difference that is important in terms of changing the physics of the conductivity of the emulsion, and the potential difference required to create a desired electric field will vary with geometry e.g. electrode spacing. Thus, whilst in a particular set-up in which the electrode spacing is not changing it is completely appropriate and somewhat simpler to consider the applied potential difference and critical potential difference, the invention may alternatively be understood in the context of applied electric field and critical electric field $E_{critical}$. In situations where the electrode spacing changes, it should be the applied electric field and critical electric field that is used to ensure consistency. Viewed from yet another aspect, the invention therefore provides a method of assessing the effect of a production chemical on the stability of a water-in-oil emulsion, comprising: adding a production chemical to the emulsion; applying an electric field across the emulsion at a detection site; measuring a current flowing through the emulsion due to the applied electric field; and using this measured current to provide an indication of the stability of the emulsion and thereby assess the effect of the production chemical. The numerous features described above in relation to other aspects of the invention are clearly also applicable to this aspect, with the discussion of applied potential difference and critical potential being interchangeable with the concept of applied electric field and critical electric field.

The assessed effect of the production chemical may be used for process control. For example, a dosage of a production chemical to be added to the emulsion or to be added to a process stream from which the emulsion is formed may be adjusted based on the determined effect of the production chemical. It will be appreciated that the production chemical to be added may be the same production chemical included in the emulsion the effect of which is being assessed, or it may be a different production chemical. Thus, the method may adjust the dosage of the same production chemical, or the assessment of the effect of the production chemical may adjust the dosage of another production chemical, a second production chemical, to be added to the emulsion or to a process stream from which the emulsion is formed.

The adjustment of a dosage may include calculating and metering a correct dosage, but may or may not include adding that adjusted dosage to the emulsion or process stream. In the case that it does not include adding the adjusted dosage to the emulsion or process stream, the method may further comprise adding the adjusted dosage of the production chemical to the emulsion or process stream.

In another embodiment, the type of production chemical may be adjusted based on the determined effect of the production chemical.

Thus, monitoring the effect of a production chemical by means of the invention enables the stability of the water and oil emulsion to be controlled.

For example, if the critical potential exceeds the reference critical potential or is above a reference window around the reference critical potential, the dosage of the production chemical to be added to the emulsion or process stream may be reduced; alternatively, if the critical potential is less than the reference critical potential or is below a reference window around the reference critical potential, the dosage of production chemical to be added to the emulsion or process stream may be increased.

In another embodiment, the step of using the measured current to provide an indication of the stability of the emulsion comprises comparing the measured current with a reference current value. Thus, a fourth aspect of the invention may be seen as providing a method of assessing the effect of a production chemical on the stability of a water and oil emulsion, the emulsion comprising the production chemical, wherein the method comprises: applying a potential difference across the emulsion at a detection site; measuring a current flowing through the emulsion due to the applied potential difference; and comparing the measured current with a reference current value to assess the effect of the production chemical.

If the measured current is greater than the reference current value or a window around the reference current value, it may be determined that the stability of the emulsion is acceptably low. Or, it may be determined that the stability is too low, and then preferably a dosage of a production chemical to be added to the emulsion or to be added to a process stream from which the emulsion is formed is then reduced. Alternatively, if the measured current is less than the reference current value or a window around the reference current value it may be determined that the stability of the emulsion is too high. Preferably a dosage of a production chemical to be added to the emulsion or to be added to a process stream from which the emulsion is formed is then increased.

In very simple terms, an embodiment of the invention may be considered as follows. A power supply connected to the electrodes sweep the potential within predefined values. Water droplets will align at a given potential, giving rise to an electric current. The potential at which this process takes place (critical potential) is registered and compared to a reference point. Alternatively, a fixed potential may be applied and the corresponding current compared with a reference value. The comparisons provide, at least indirectly, an assessment of the effect of the production chemical.

By means of embodiments of the invention the dosage of a production chemical to be added to the emulsion or process stream can be adjusted so as to optimise the stability of the emulsion. Thus, viewed from a fifth aspect, the invention can be seen as providing a method of optimising the stability of a water and oil emulsion, comprising: adding a production chemical to the emulsion or to a process stream from which the emulsion is formed; applying a potential difference across the emulsion at a detection site; measuring a current flowing through the emulsion due to the applied potential difference; using this measured current to assess the effect of the production chemical; adjusting a dosage of a production chemical to be added to the emulsion based on the determined effect of the production chemical; and adding the adjusted dosage of production chemical to the emulsion or a process stream from which the emulsion is formed.

The production chemical to be added to the emulsion or process stream may be added upstream and/or downstream of the detection site. Where the production chemical is added upstream, one can measure the effect of the production chemical and control further according to the measured response.

Typically, the emulsion may be flowing in a pipe. A first electrode of the pair of electrodes may be mounted on a wall of the pipe. A second electrode of the pair of electrodes may be mounted on the wall of the pipe and radially offset from the first electrode; and/or mounted on the wall of the pipe and axially offset from the first electrode; and/or provided within the emulsion.

In some embodiments, the method may further comprise regulating the flow of the emulsion upstream of the detection site, preferably using a valve or flow regulating device or flow alteration device.

In one particular embodiment, the emulsion is diverted from a main emulsion flow path and the detection site is on this diverted flow path.

Whilst embodiments of the invention allow the optimisation of the emulsion stability through dosage adjustment of a production chemical, embodiments are also envisaged in which the emulsion stability is not optimised through dosage adjustment. In such embodiments, the methodology of the invention may be used to simply characterize the response of different production chemicals through assessing their effect on the stability of an emulsion and changes in the behaviour of an emulsion due to interference with other additives. Hence the methodology could be used to determine the reference critical potential of an emulsion to which a production chemical has been added.

The invention further extends to an apparatus configured to carry out any of the above described methods. In particular, viewed from a sixth aspect, the invention provides an apparatus for assessing the effect of a production chemical on the stability of a water and oil emulsion comprising the production chemical, the apparatus comprising: a pair of electrodes configured to be arranged across the emulsion at a detection site; a power source connected across the pair of electrodes and configured to apply a potential difference across the pair of electrodes; and a processing unit; wherein the processing unit is configured to: measure the current flowing through the emulsion due to the applied potential difference, and use this measured current to provide an indication of the stability of the emulsion and thereby the effect of the production chemical.

It will be appreciated that the critical potential of the emulsion is dependent on the spacing between the electrodes. Thus, the critical potential of the emulsion with added production chemical may vary depending on the setup of the electrodes. The critical electric field strength is constant regardless of the electrode spacing. However, the critical potential may be used as an indicator of emulsion stability since the electrode spacing is known.

The apparatus is easy to implement and does not require sophisticated equipment.

The apparatus may be provided across a pipe carrying the emulsion. The apparatus may therefore be retrofit or installed over an existing pipe.

A first electrode of the pair of electrodes may be mounted on a wall of the pipe. A second electrode of the pair of electrodes may be mounted on the wall of the pipe and radially offset from the first electrode; and/or mounted on the wall of the pipe and axially offset from the first electrode; and/or provided within the emulsion. The apparatus may therefore be installed in any suitable manner depending on the location of the detection site.

The apparatus may further comprise one or more additional pairs of electrodes configured to be arranged across the emulsion at the detection site. For example, one pair of electrodes may be arranged horizontally at the detection site, while a second pair of electrodes may be arranged perpendicular to the first pair of electrodes. The or another power source would preferably be connected across the additional pair(s) of electrodes to apply a potential difference across the additional pair(s) of electrodes, and the processing unit would preferably measure the current flowing due to the potential difference applied by all pairs of electrodes. In this way, stratification of the flow of emulsion may be accounted for.

Also provided is a pipe for carrying an emulsion comprising the above described apparatus, and a crude oil processing system comprising such a pipe.

The detection site may be located at a by-pass section of the pipe. A valve or a flow-modifying or flow alteration device may be provided upstream of the detection site. In doing, the flow of the emulsion may be more controlled as it reaches the detection site.

The detection site may be located upstream of a pump. In this way, the stability of the emulsion upstream of the pump may be determined, in order to ensure a proper understanding of the fluid behaviour entering the pump. The detection site may alternatively be located downstream of a pump. Pumps may have a tendency to generate emulsions. The stability of an emulsion leaving a pump can thus be determined in order to understand the fluid behaviour exiting the pump.

It will be readily appreciated by the skilled person that the various optional and preferred features of embodiments of the invention described above are applicable to all of the various aspects of the invention discussed. So that those skilled in the art to which the invention appertains will readily understand how to make and use the devices and methods of the invention without undue experimentation, embodiments thereof will be described in detail herein below by way of example only and with reference to certain figures, wherein:

FIG. 4 is a graph of critical potential in volts (V) v. concentration of emulsion breaker for an exemplary embodiment. Reference will now be made to the drawings wherein like reference numerals identify similar structural features or aspects of the subject disclosure. For purposes of explanation and illustration, and not limitation, an illustrative view of an embodiment of an apparatus for assessing the effect of a production chemical on the emulsion stability of a water-in-oil crude oil emulsion is shown in FIG. 1 and is designated generally by reference character 100. Other embodiments are shown in FIGS. 2A to 4. The production chemical is typically an emulsion breaker, but may be any production chemical that has an effect on the stability of the emulsion.

Figure 1:
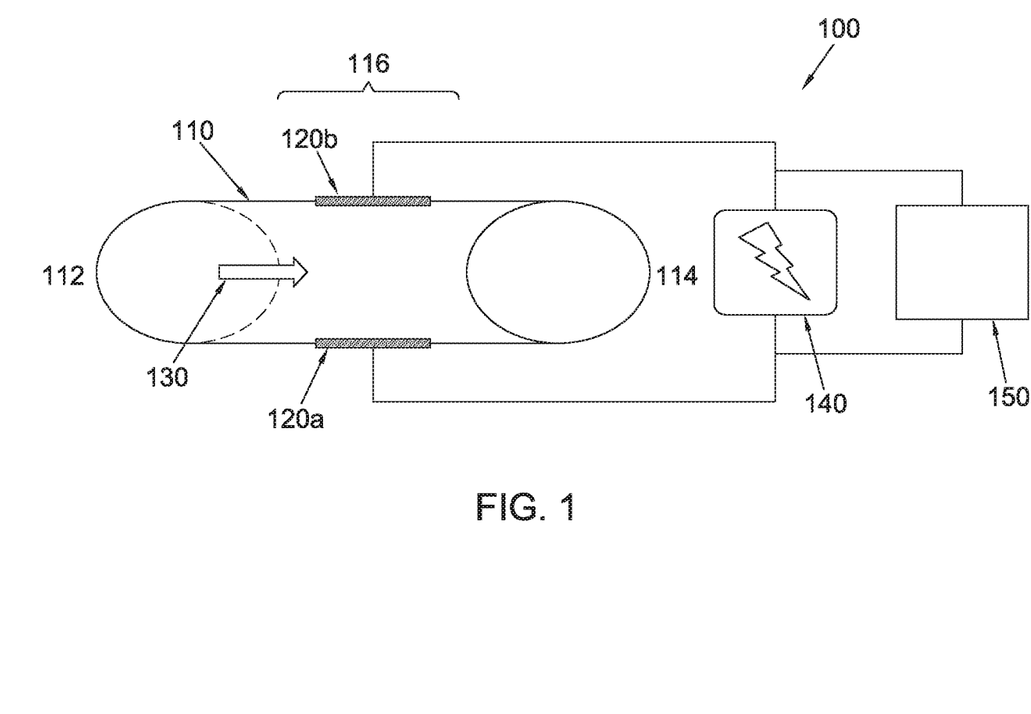
FIG. 1 illustrates an exemplary embodiment of an apparatus for assessing the effect of a production chemical on a water-in-oil emulsion.

The apparatus 100 comprises a pair of electrodes 120$a$, 120$b$ to be provided across a crude oil emulsion at a detection site 116. A first electrode 120$a$ of the pair of electrodes 120$a$, 120$b$ is arranged such that it is generally parallel with a second electrode 120$b$ of the pair of electrodes. The apparatus 100 is provided on a pipe 110. The first electrode 120$a$ is provided on the wall of the pipe 110. The second electrode 120$b$ is provided on the wall of the pipe 110, radially offset and generally opposite the first electrode 120$a$.

The emulsion may be stagnant, or may be permitted to flow within the pipe 110 carrying the crude oil emulsion and a production chemical. Where the emulsion is permitted to flow, the flow direction 130 of the emulsion may be generally from an upstream side 112 of the detection site 116 to a downstream side 114 of the detection site 116. A production chemical, for example an emulsion breaker, is added to the emulsion upstream 112 and/or downstream 114 of the detection site 116.

The pair of electrodes 120a, 120b is connected to a power source 140. The power source 140 provides a voltage, either an AC or DC voltage (potential difference), or a combination thereof. In preferred embodiments, a DC potential difference is applied. The power source 140 may provide a fixed potential difference or may provide a variable potential difference. The maximum potential difference applied across the pair of electrodes 120a, 120b may vary depending on the application but it is likely to be limited to less than 10,000V, and may typically be below 1000V, due to the risk of sparks at higher voltages. The electrodes may be formed of any suitable material; for many systems, stainless steel may be suitable, but for more aggressive environments one may consider noble metals, noble metal oxides, carbon and/or lead.

A processing unit 150 is provided across the pair of electrodes 120a, 120b. The processing unit 150 is configured to control the power source 140 and measure a current flowing between the pair of electrodes 120a, 120b.

The processing unit 150 may store the value of a potential difference, or a series of potential differences, applied across the pair of electrodes 120a, 120b, and further may store the corresponding measured current value(s). It may be configured to carry out various calculations such as the determination of the critical potential (discussed later)

The processing unit 150 may store one or more reference characteristics. The reference characteristic(s) may be potential or current value(s) which may be representative of a preferred emulsion stability. The processing unit 150 may store reference emulsion stability characteristics for different types of emulsion and production chemical and the different combinations of differing emulsions and production chemicals.

The processing unit 150 may be connected to a display (not shown), which is configured to display to an operator various measured and calculated values, such as the critical potential of the emulsion being assessed and how this compares with a reference value.

The processing unit 150 is configured to determine and control the amount of emulsion breaker to be added to the emulsion upstream 112 and/or downstream 114 of the detection site 116, based on the measured current values, as discussed later.

The detection site 116 may be located at any stage of the crude oil processing line. The apparatus 100 may be installed in the wells, the pipeline or in process equipment (for example, at or in a separator).

A first method of using the apparatus 100 of FIG. 1 to assess the effect of the emulsion breaker will now be described. This method utilises a measured current value to determine if the critical potential has been reached. An emulsion breaker is added to the emulsion at a point upstream 112 of the detection site 116. The emulsion with added breaker then flows through pipe 110 to the detection site 116. The power supply 140 applies a potential difference across the first 120a and second 120b electrodes. The processing unit 150 then measures and records the potential difference across and the current flowing between the first 120a and second 120b electrodes. The processing unit 150 calculates the difference between the recorded current and a reference current to provide a current variance value. The reference current is a fixed value that is stored in the processing unit 150 beforehand and is representative of a critical potential being applied.

If the recorded current is greater than or equal to the reference current i.e. the current variance value is nil or positive, it is determined that the potential difference applied across the first 120a and second 120b electrodes is at or above the critical potential of the emulsion. If the recorded current is less than the reference current i.e. the current variance value is negative, it is determined that the potential difference applied across the first 120a and second 120b electrodes is below the critical potential of the emulsion.

If it has been determined that the potential difference applied across the first 120a and second 120b electrodes is below the critical potential of the emulsion being characterised, the potential difference applied to the first 120a and second 120b electrodes is then increased and the above process repeated until it is determined that the current variance value is nil or positive. The potential difference applied across the first 120a and second 120b electrodes may be increased by an interval in the range of 1-100V (i.e. in steps of 1-100V). In other words, a range of potential differences are "swept" in a stepwise manner in order to determined when the critical potential has been reached.

If it has been determined that the potential difference applied across the first 120a and second 120b electrodes is at or above the critical potential of the emulsion, the potential difference applied across the first 120a and second 120b electrodes is stored in the processing unit 150 as a measured critical potential.

The measured critical potential is then compared to a reference critical potential. The processing unit 150 calculates the difference between the measured critical potential and the reference critical potential and stores this value as a critical potential error. This error is then used to adjust the dosage of the emulsion breaker, added to the emulsion upstream 112 or downstream 114 of the detection site 116.

For example, if the measured critical potential is greater than the reference critical potential i.e. the critical potential error is positive, it is determined that the stability of the emulsion is too high. The dosage of the emulsion breaker to be added to the emulsion is then increased.

On the other hand, if the measured critical potential is less than the reference critical potential i.e. the critical potential error is negative, it is determined that the stability of the emulsion is too low and the dosage of emulsion breaker to be added to the emulsion may be decreased in the manner described above. Alternatively, it may be determined that the low stability of the emulsion is suitable for processing purposes, and so the dosage of emulsion breaker is not adjusted. This may depend on the magnitude of the critical potential error.

If the measured critical potential is equal to the reference critical potential i.e. the critical potential error is zero, or is within a certain range of the reference critical potential, it is determined that the stability of the emulsion is at or within the desired range. There may then be no requirement to adjust the dosage of the breaker being added to the emulsion.

A second method of using the apparatus 100 of FIG. 1 to assess the effect of the emulsion breaker will now be described. This method is similar to that of the first method described above except that instead of utilising a measured current value, it utilises a measured rate of change of current flowing to determine if the critical potential has been reached. A particular rate of change of current may be indicative of a critical potential being reached since the current increases significantly once the critical potential is reached. An emulsion breaker is added to the emulsion at a point upstream 112 of the detection site 116. The emulsion with added breaker then flows through pipe 110 to the detection site 116. The power supply 140 applies a first potential difference across first 120a and second 120b electrodes. The processing unit 150 measures and records the potential difference applied across the first 120a and second 120b electrodes and the corresponding current flowing between the electrodes.

The potential difference applied across the first 120a and second 120b electrodes is then increased to a second potential difference, resulting in a new electric field being applied across the emulsion. The potential difference applied across the first 120a and second 120b electrodes may be increased by an interval in the range of 1-100V (i.e. in steps of 1-100V). The processing unit 150 measures and records the potential difference applied across the first 120a and second 120b electrodes and the corresponding current flowing through the emulsion. The processing unit 150 then calculates the change in current from the first potential difference to the second potential difference with respect to the change in potential difference, in order to find a rate of change of current.

If this calculated current value is less than a reference rate of change value (the reference rate of change value being indicative of a critical potential being applied), it is determined that the second potential difference applied is not at the critical potential of the emulsion. The potential difference applied to the first 120a and second 120b electrodes is then increased and the above process repeated until the calculated value is greater than or equal to the reference rate of change value. In other words, a range of potential differences are "swept" in a stepwise manner in order to find the critical potential.

If, however, the calculated current value is greater than or equal to the reference rate of change value, it is determined that the second potential difference applied is at or greater than the critical potential of the emulsion.

The critical potential of the emulsion may be set to be the arithmetic mean of the first and second potential differences, and stored in the processing unit 150 as a measured critical potential. Alternatively, the measured critical potential may be set to be equal to the second potential difference applied.

The measured critical potential is then compared to a reference critical potential. The processing unit 150 calculates the difference between the measured critical potential and the reference critical potential and stores this value as a critical potential error. This error is then used to adjust the dosage of the emulsion breaker, added to the emulsion upstream 112 or downstream 114 of the detection site 116, as described above.

A third method of using the apparatus 100 of FIG. 1 will now be described. In this method, the $V_{critical}$ is not actually calculated The emulsion breaker is added to the emulsion at a point upstream 112 of the detection site 116. The emulsion with added breaker flows through pipe 110 to the detection site 116. The power supply 140 applies a fixed potential difference across first 120a and second 120b electrodes. The processing unit 150 measures and records the potential difference applied across the first 120a and second 120b electrodes and the corresponding current flowing through the emulsion. The measured current is compared to a reference current indicative of a desired emulsion stability (this may e.g. be the current at which the critical potential is applied, but the critical potential itself is not actually calculated)

If the measured current is equal to the reference current, it is determined that the conductivity of the emulsion and thus the stability of the emulsion is at a desired level or within a desired range. Adjustment of the dosage the emulsion breaker, added to the emulsion may not be required.

If the measured current is greater than the reference current, it is determined that the conductivity of the emulsion is too high and thus the stability of the emulsion is too low. The dosage of emulsion breaker to be added to the emulsion may be decreased in the manner described above in order to increase the stability of the emulsion. Or, it may be determined that the low stability of the emulsion is suitable, and so the dosage of the emulsion breaker is not adjusted. This may depend on the magnitude of the difference between the measured current and the reference current.

If the measured current is less than the reference current, it is determined that the conductivity is too low such that the stability of the emulsion is too high. The dosage of emulsion breaker to be added to the emulsion upstream 112 or downstream 114 of the detection site 116 may then be adjusted (i.e. increased), as described above, to reduce the stability of the emulsion.

The above process may be repeated i.e. the processing unit 150 may continually monitor the current between the first 120a and second 120b electrodes in order to determine whether the stability of the emulsion is too low, too high or at the desired level. In this way, the dosage of the emulsion breaker to be added to the emulsion may be adjusted as necessary, in order to ensure that the stability of the emulsion is at or below the desired level.

For each of the above methods, once the dosage of the production chemical (e.g. emulsion breaker) to be added to the emulsion has been adjusted, the adjusted dose of production chemical is then added to the emulsion.

Each of the above methods describes the adjustment of dosage of the production chemical, e.g. emulsion breaker, originally added to the emulsion. However, in other embodiments, another production chemical may be adjusted based on whether it is determined that the stability of the emulsion is too high or too low. For example, if it is determined that the stability of the emulsion is too high, another production chemical, e.g. another emulsion breaker, may also be added to correct the stability of the emulsion (or the dosage of this other emulsion breaker may be increased). Equally, if it is determined that the stability of the emulsion is too low, the dosage of a different production chemical e.g. a different emulsion breaker being added to the emulsion is reduced.

Furthermore, instead of adjusting the dosage of a production chemical (either the one originally added or a different one), the type of production chemical may be changed in order to correct the stability of the emulsion. For example, if it is determined that the stability of the emulsion is too high, the production chemical originally added may be changed to one which creates a stronger destabilisation effect. Equally, if it is determined that the stability of the emulsion is too low, the production chemical originally added may be changed to one which creates a weaker destabilisation effect. Or, if it is determined that the stability of the emulsion is at the desired level, then the type of production chemical is not changed.

The production chemical may be added upstream or downstream of the detection site.

The steps of adjusting the dosage of production chemical and adding the production chemical to the emulsion may be fully automated and controlled by the processing unit 150. Alternatively, for facilities with manual control, the critical potential of the emulsion being assessed and/or its comparison with a reference value may be indicated to the operator via the display. The operator may then manually determine how the dosage of a production chemical (either the one originally added or a different one) should be adjusted, and then adjust the dosage accordingly and add it to the emulsion. It will be appreciated that any one or more steps of any of the above methods may be performed manually.

Figure 2A:
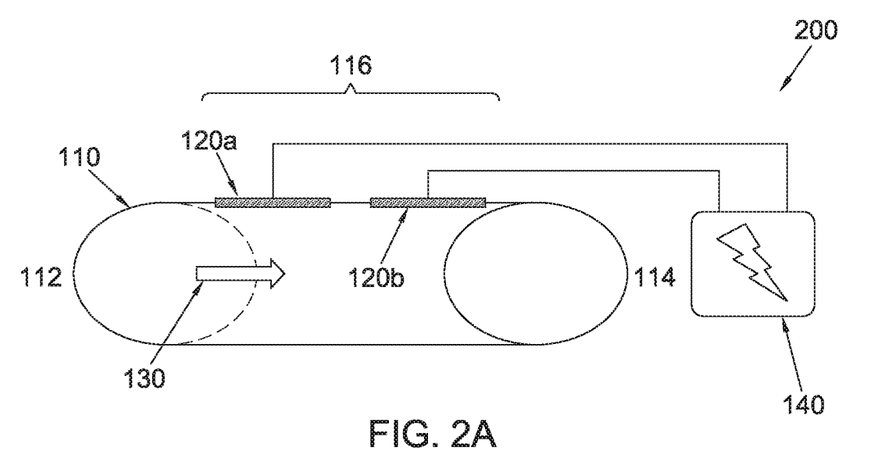
FIG. 2A illustrates an alternative exemplary embodiment of an apparatus for assessing the effect of a production chemical on a water-in-oil emulsion.

FIG. 2A shows an alternative apparatus 200 for assessing the effect of a production chemical on the emulsion stability of a crude oil emulsion according to an embodiment of the invention. A first electrode 120a may be provided on the wall of the pipe 110, and a second electrode 120b may be provided adjacent the first electrode 120a such that it is axially offset from the first electrode 120a in a direction generally in line with the flow direction 130 of the emulsion. The methods described above for assessing the effect of a production chemical on a crude oil emulsion may be employed using apparatus 200.

Figure 2B:
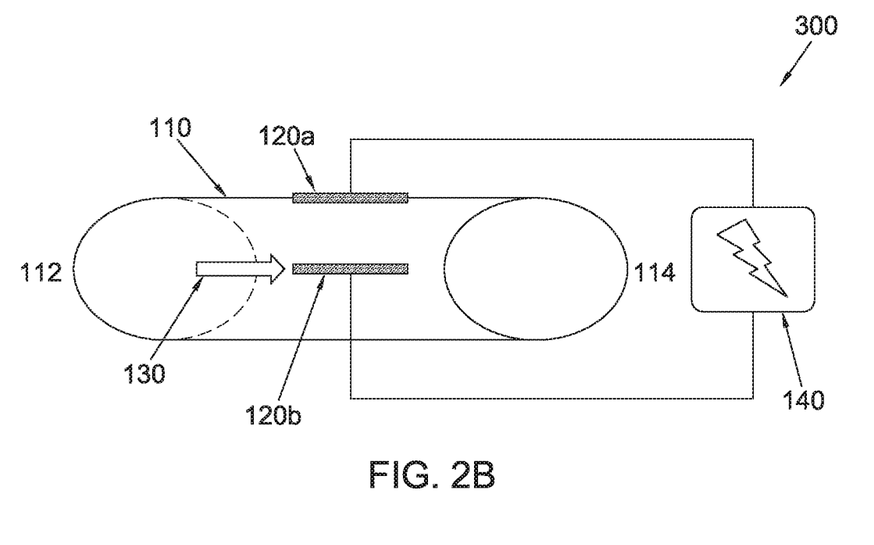
FIG. 2B illustrates an alternative exemplary embodiment of an apparatus for assessing the effect of a production chemical on a water-in-oil emulsion.

FIG. 2B shows a further alternative apparatus 300 assessing the effect of a production chemical on the emulsion stability of a crude oil emulsion according to an embodiment of the invention. A first electrode 120a may be provided on the wall of the pipe 110, and a second electrode 120b may be provided within the pipe 110 such that it is within the emulsion. The methods described above for assessing the effect of a production chemical on the emulsion stability of a crude oil emulsion may be employed using apparatus 300.

Figure 3:
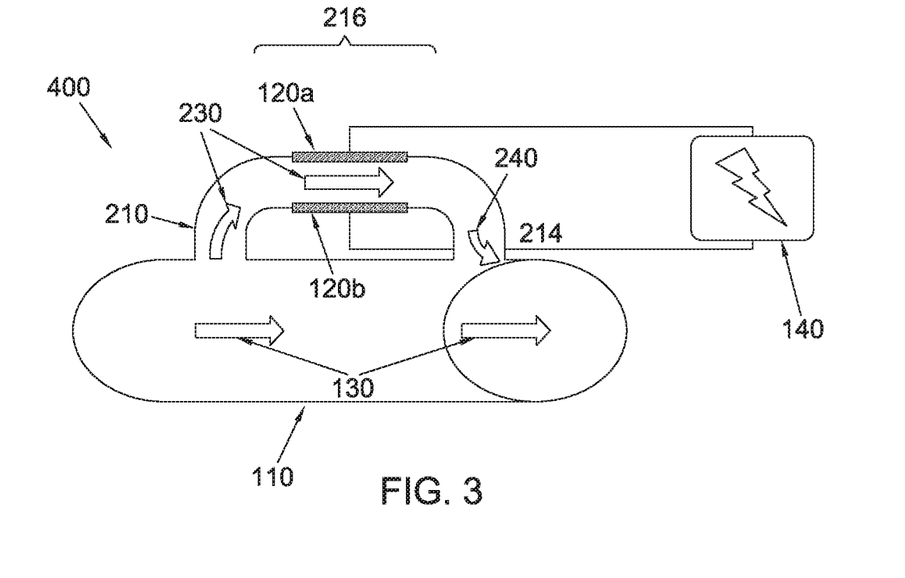
FIG. 3 illustrates an alternative exemplary embodiment of an apparatus for assessing the effect of a production chemical on a water-in-oil emulsion.

FIG. 3 shows yet another alternative apparatus 400 for assessing the effect of a production chemical on the emulsion stability of a crude oil emulsion. A by-pass section 210 may be provided across pipe 110. A flow 230 of emulsion to be characterised may be diverted from the pipe 110 and flow into the by-pass section 210. The apparatus 100, 200, 400 as described above may be provided across the by-pass section 210 (instead of across the pipe itself as in those earlier embodiments). Downstream 214 of the detection site 216, the emulsion may return to the pipe 110 via flow path 240. The methods described above for assessing the effect of a production chemical on the emulsion stability of a crude oil emulsion may be employed using apparatus 400.

Optionally, a valve or flow regulating/alteration device (for example a swirl element) may be provided upstream of the detection site 116, 216 in order to regulate the flow of the emulsion before it reaches the detection site 116, 216.

It can clearly be understood that the above described apparatuses do not just enable assessment of the effect of a production chemical on a water-in-oil emulsion, but also the optimisation of the emulsion stability through dosage adjustment of a production chemical. Thus, the apparatuses and methods of embodiments of the invention may be considered as ones providing optimisation of the emulsion stability of a water-in-oil emulsion.

However, embodiments are also envisaged in which the emulsion stability is not optimised. Rather, the effect of the production chemical is assessed simply in order to characterise the response of the production chemical. Different additives may be added to the emulsion, and any resulting change in effect of the production chemical assessed.

Figure 4:
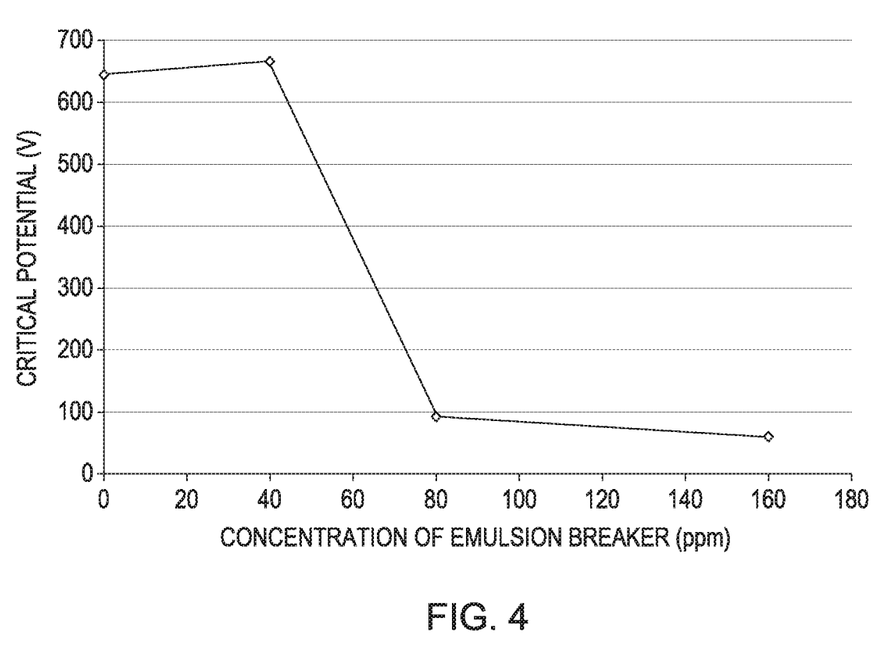

FIG. 4 is a graph of critical potential v. concentration of emulsion breaker for an exemplary embodiment of the invention. This graph illustrates the concept that as the concentration of emulsion breaker increases (and thus stability of the emulsion reduces), the critical potential will reach a point (here, approximately 660V) when it suddenly reduces. Thus, at this point, the stability of the emulsion has reduced to a point where the water droplets are easily aligned by the applied potential, and current can flow. The potential required to do this (i.e. the critical potential) then reduces since the emulsion is adequately "broken" by the breaker, i.e. is unstable enough to allow current to flow easily.

Whilst the embodiments described above are described in terms of an applied potential difference, as will be appreciated from the earlier description in this application, it is the electric field created by the applied potential difference that is important in terms of the changing the physics of the conductivity of the emulsion, in other words the destabilisation of the emulsion is caused by the electric field. The potential difference required to create a desired electric field will vary with geometry e.g. electrode spacing. In a particular set-up in which the electrode spacing is not changing, such as in the embodiments described above, it is completely appropriate and somewhat simpler to consider the applied potential difference and critical potential difference. However, instead of considering the application of potential difference and a critical potential difference $V_{critical}$, the above embodiments may alternatively be understood in the context of applied electric field and critical electric field $E_{critical}$. In situations where the electrode spacing changes, it should be the applied electric field and critical electric field that is used to ensure consistency.

While the apparatus and methods of the subject disclosure have been shown and described with reference to embodiments, those skilled in the art will readily appreciate that changes and/or modifications may be made thereto without departing from the scope of the subject disclosure.

The invention claimed is:

1. A method of assessing the effect of a production chemical on the stability of a water and oil emulsion, the emulsion comprising the production chemical, wherein the method comprises:
   providing a water and oil emulsion flowing in a pipe;
   subsequently adding the production chemical to the emulsion upstream of a detection site;
   applying a potential difference across the emulsion at the detection site;
   measuring a current flowing through the emulsion due to the applied potential difference; and
   using this measured current to provide an indication of the stability of the emulsion and thereby assess the effect of the production chemical.

2. A method as claimed in claim 1, wherein the step of using the measured current to provide an indication of the stability of the emulsion includes determining, based on the measured current, whether a critical potential of the emulsion has been reached or exceeded.

3. A method as claimed in claim 2, wherein the measured current is compared with a reference current corresponding to the critical potential, and if the measured current is greater than or equal to the reference current it is determined that the critical potential of the emulsion has been reached or exceeded; and if the measured current is less than the reference current it is determined that the critical potential has not been reached.

4. A method as claimed in claim 2, wherein after the step of measuring the current flowing through the emulsion, the method further comprises:
   increasing the potential difference across the emulsion;
   measuring the current flowing through the emulsion due to the increased potential difference;
   determining the rate of change of current with respect to potential difference;

comparing the determined rate of change to a reference rate of change value;

and if the measured rate of change is greater than or equal to the reference rate of change, it is determined that the critical potential of the emulsion has been reached or exceeded; and if the measured rate of change is less than the reference rate of change it is determined that the critical potential has not been reached.

5. A method as claimed in claim 2, wherein if it has been determined that the critical potential of the emulsion has not been reached, the method further comprises increasing the potential difference across the emulsion at the detection site, and repeating the steps of:

measuring a current flowing through the emulsion due to the applied potential difference; and using this measured current to provide an indication of the stability of the emulsion; by determining, based on the measured current, whether a critical potential of the emulsion has been reached or exceeded.

6. A method as claimed in claim 5, wherein the method is repeated until the critical potential has been reached or exceeded.

7. A method as claimed in claim 1, wherein if it has been determined that the critical potential of the emulsion has been reached or exceeded, the method further comprises:

determining the critical potential based on the applied potential difference at the time when it was determined that the critical potential has been reached or exceeded; and comparing the critical potential of the emulsion with a reference critical potential to provide an indication of the stability of the emulsion and thereby the effect of the production chemical.

8. A method as claimed in claim 1, further comprising adjusting a dosage of a production chemical to be added to the emulsion or to be added to a process stream from which the emulsion is formed, based on the determined effect of the production chemical;

or adjusting the type of production chemical to be added to the emulsion or to a process stream from which the emulsion is formed, based on the determined effect of the production chemical.

9. A method as claimed in claim 1, wherein the step of using the measured current to provide an indication of the stability of the emulsion comprises comparing the measured current with a reference current value.

10. A method as claimed in claim 1, wherein the emulsion is a crude oil emulsion and/or wherein the emulsion is a water-in-oil emulsion.

11. A method as claimed in claim 1, further comprising regulating the flow of the emulsion upstream of the detection site, preferably using a valve or flow regulating device or flow alteration device.

12. A method as claimed in claim 1, wherein the emulsion is diverted from a main emulsion flow path and the detection site is on this diverted flow path.

13. An apparatus configured to carry out the method as claimed in claim 1.

14. An apparatus for assessing the effect of a production chemical on a water and oil emulsion comprising the production chemical, the apparatus comprising:

a pair of electrodes configured to be arranged across the emulsion comprising the production chemical at a detection site, wherein the production chemical is added upstream of the detection site;

a power source connected across the pair of electrodes and configured to apply a potential difference across the pair of electrodes; and a processing unit;

wherein the processing unit is configured to: measure the current flowing through the emulsion due to the applied potential difference, and use this measured current to provide an indication of the stability of the emulsion and thereby the effect of the production chemical; and wherein the apparatus is configured to be provided across a pipe carrying the emulsion.

15. An apparatus as claimed in claim 14, wherein a first electrode of the pair of electrodes is configured to be mounted on a wall of the pipe.

16. An apparatus as claimed in claim 14, further comprising one or more additional pair(s) of electrodes configured to be arranged across the emulsion at the detection site.

17. The or apparatus of claim 14, wherein the production chemical is an emulsion breaker, corrosion inhibitor, biocide or scale inhibitor.

18. A pipe for carrying an emulsion, comprising an apparatus as claimed in claim 14.

* * * * *